US00PP14883P2

(12) United States Plant Patent
Post

(10) Patent No.: US PP14,883 P2
(45) Date of Patent: Jun. 8, 2004

(54) CHRYSANTHEMUM PLANT NAMED 'ANNECY RED'

(50) Latin Name: *Chrysanthemum×morifolium*
Varietal Denomination: Annecy Red

(75) Inventor: Arie Gerard Post, 's-Gravenzande (NL)

(73) Assignee: Deliflor Royalties, B.V., Maasdijk (NL)

( * ) Notice: Subject to any disclaimer, the term of this patent is extended or adjusted under 35 U.S.C. 154(b) by 0 days.

(21) Appl. No.: 10/654,394

(22) Filed: Sep. 2, 2003

(51) Int. Cl.[7] ..... A01H 5/00
(52) U.S. Cl. ..... Plt./298
(58) Field of Search ..... Plt./298

*Primary Examiner*—Anne Marie Grunberg
(74) *Attorney, Agent, or Firm*—C. A. Whealy

(57) ABSTRACT

A new and distinct cultivar of Chrysanthemum plant named 'Annecy Red', characterized by its anemone type inflorescences with spooned red purple-colored ray and red-colored disc florets; strong and erect flowering stems; early flowering response; good postproduction longevity; and resistance to Chrysanthemum White Rust.

1 Drawing Sheet

Botanical classification/cultivar designation: *Chrysanthemum×morifolium* cultivar Annecy Red.

BACKGROUND OF THE INVENTION

The present invention relates to a new and distinct cultivar of Chrysanthemum plant, botanically known as *Chrysanthemum×morifolium* and referred to by the name 'Annecy Red'.

The new Chrysanthemum is a naturally occurring whole plant mutation of the Chrysanthemum cultivar Annecy, not patented. The new Chrysanthemum was discovered and selected by the Inventor on Aug. 30, 2000 within a population of plants of the cultivar Annecy in a controlled environment in 's Gravenzande, The Netherlands.

Asexual reproduction of the new Chrysanthemum by terminal cuttings in 's Gravenzande, The Netherlands since Oct. 10, 2000, has shown that the unique features of this new Chrysanthemum are stable and reproduced true to type in successive generations.

BRIEF SUMMARY OF THE INVENTION

The cultivar Annecy Red has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Annecy Red'. These characteristics in combination distinguish 'Annecy Red' as a new and distinct cultivar:

1. Anemone type inflorescences with spooned red purple-colored ray and red-colored disc florets; typically grown as a spray type.
2. Strong and erect flowering stems.
3. Early flowering response.
4. Good postproduction longevity.
5. Resistant to Chrysanthemum White Rust.

Plants of the new Chrysanthemum differ from plants of the parent, the cultivar Annecy, primarily in ray floret coloration as plants of the cultivar Annecy have light pink-colored ray florets.

Plants of the new Chrysanthemum differ from plants of the cultivar Annecy Lemon, disclosed in a U.S. Plant Patent application No. 10/654,395, primarily in ray and disc floret coloration.

Plants of the new Chrysanthemum can be compared to plants of the Chrysanthemum cultivar Yellow Bijoux, disclosed in U.S. Plant Pat. No. 8,329. In side-by-side comparisons conducted in 's Gravenzande, The Netherlands, plants of the new Chrysanthemum differed from plants of the cultivar Yellow Bijoux in the following characteristics:

1. Plants of the new Chrysanthemum were stronger growing than plants of the cultivar Yellow Bijoux.
2. Plants of the new Chrysanthemum flowered earlier than plants of the cultivar Yellow Bijoux.
3. Plants of the new Chrysanthemum were more freely flowering than plants of the cultivar Yellow Bijoux.
4. Plants of the new Chrysanthemum had larger inflorescences than plants of the cultivar Yellow Bijoux.
5. Plants of the new Chrysanthemum were resistant to Chrysanthemum White Rust whereas plants of the cultivar Yellow Bijoux were susceptible to Chrysanthemum White Rust.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph at the top of the sheet comprises a side perspective view of a typical flowering stem of 'Annecy Red'.

The photograph at the bottom of the sheet comprises a close-up view of typical leaves and inflorescences of 'Annecy Red'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the spring in 's Gravenzande, The Netherlands, under commercial practice in a glass-covered greenhouse. Plants were initially given long day/short night treatments followed by short day/long night treatments to induce flower initiation and development. During the production of the plants, day temperatures were about 18° C. and night temperatures were about 17° C. Plants were about ten weeks from planting when the photographs and the description were taken.

Botanical classification: *Chrysanthemum×morifolium* cultivar Annecy Red.

Commercial classification: Anemone type Chrysanthemum typically grown as a spray-type cut flower.

Parentage: Naturally occurring whole plant mutation of *Chrysanthemum×morifolium* cultivar Annecy, not patented.

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 10 days at 20° C.

*Time to produce a rooted cutting, winter.*—About 14 days at 18° C.

*Root description.*—Fine and freely branching; white in color.

Plant description:

*Appearance.*—Herbaceous anemone-type cut Chrysanthemum; typically grown as a spray type; erect and strong flowering stems.

*Growth rate.*—Moderate; vigorous.

*Flowering stem description.*—Length: About 90 to 100 cm. Diameter, at apex: About 6 mm. Internode length: About 4 cm. Strength: Strong. Aspect: Erect. Branching habit: Plants are typically grown as single stems; if pinched, plants will produce about 12 lateral branches. Color: 138B.

*Foliage description.*—Arrangement: Alternate. Length: About 9 to 14 cm. Width: About 4 to 10 cm. Apex: Acute. Base: Acute. Margin: Pinnately lobed. Texture: Rough; both surfaces pubescent. Petiole length: About 3 to 4 cm. Petiole diameter: About 2 to 3 mm. Color: Developing and fully expanded foliage, upper surface: 147A. Developing and fully expanded foliage, lower surface: 137C. Venation, upper surface: 146B. Venation, lower surface: 137C. Petiole, upper surface: 137A. Petiole, lower surface: 137C.

Inflorescence description:

*Appearance.*—Anemone type inflorescence form with spooned-shaped ray florets. Inflorescences borne on terminals above foliage. Disk and ray florets develop acropetally on a capitulum. Not fragrant. Typically grown as a spray type, but can also be grown as a standard type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 47 to 49 days later.

*Postproduction longevity.*—Inflorescences will maintain good substance and form for about 18 days after harvesting.

*Quantity of inflorescences per flowering stem.*—About 15 to 18 inflorescences per flowering stem.

*Inflorescence size.*—Diameter: About 8 to 10 cm. Depth (height): About 4 to 6 cm.

*Inflorescence buds.*—Length: About 5 mm. Diameter: About 1 cm. Shape: Oblate. Color: 138A.

*Ray florets.*—Length, fully developed: About 5 to 5.5 cm. Width, fully developed: About 3 mm. Shape: Tubular with spooned apices. Apex: Retuse. Base: Fused. Margin: Entire. Texture: Smooth, glabrous. Number of ray florets per inflorescence: About 55. Color: When opening, upper surface: 59C. When opening, lower surface: Closest to 84C. Fully opened, upper surface: 59D; color becoming closer to 84C with development. Fully opened, lower surface: Closest to 84C.

*Disc florets.*—Shape: Elongated tubular. Length: About 0.5 to 5 cm. Width: About 1 to 3 mm. Number of disc florets per inflorescence: About 300. Color: Immature: 69B. Mature: Apex: 46A. Mid-section: 51D. Base: 145D.

*Peduncles.*—Length, terminal peduncle: About 4 cm. Length, fourth peduncle: About 11 to 12 cm. Diameter: About 2 to 4 mm. Angle: About 45° from vertical. Texture: Pubescent. Color: 138B.

*Reproductive organs.*—Androecium: Present on disc florets only. Anther color: 165B. Pollen: None observed. Gynoecium: Present on both ray and disc florets.

*Seed/fruit.*—Seed and fruit production has not been observed.

Disease/pest resistance: Plants of the new Chrysanthemum have been observed to be resistant to Chrysanthemum White Rust. Plants of the new Chrysanthemum have not been observed to be resistant to other known pathogens and pests common to Chrysanthemum.

It is claimed:

1. A new and distinct cultivar of Chrysanthemum plant named 'Annecy Red', as illustrated and described.

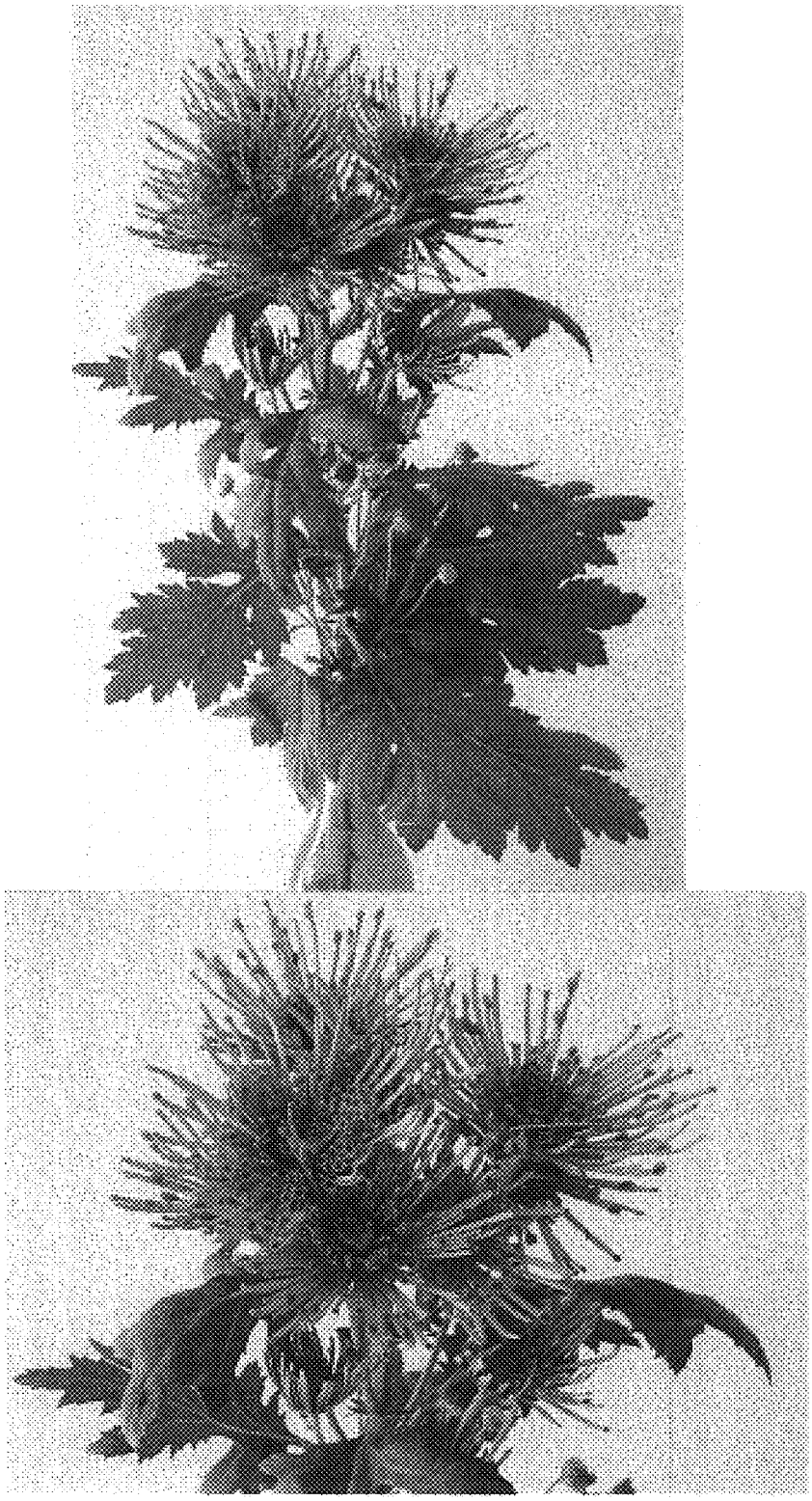

* * * * *